(12) United States Patent
Murakami et al.

(10) Patent No.: US 12,029,797 B2
(45) Date of Patent: Jul. 9, 2024

(54) FATTY ACID DERIVATIVE LABELED WITH POSITRON-EMITTING RADIONUCLIDE

(71) Applicant: ASTELLAS PHARMA INC., Tokyo (JP)

(72) Inventors: Yoshihiro Murakami, Tokyo (JP); Hiroshi Fushiki, Tokyo (JP); Yuji Fujita, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 781 days.

(21) Appl. No.: 17/261,328

(22) PCT Filed: Jul. 19, 2019

(86) PCT No.: PCT/JP2019/028380
§ 371 (c)(1),
(2) Date: Jan. 19, 2021

(87) PCT Pub. No.: WO2020/017620
PCT Pub. Date: Jan. 23, 2020

(65) Prior Publication Data
US 2021/0338845 A1     Nov. 4, 2021

(30) Foreign Application Priority Data
Jul. 20, 2018 (JP) .................................. 2018-136483

(51) Int. Cl.
*A61K 51/04* (2006.01)
*C07B 59/00* (2006.01)

(52) U.S. Cl.
CPC ........ *A61K 51/0402* (2013.01); *C07B 59/001* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 4,323,547 | A | 4/1982 | Knust et al. |
| 6,362,352 | B1 | 3/2002 | DeGrado et al. |
| 2004/0253177 | A1 | 12/2004 | Elmaleh et al. |
| 2016/0185735 | A1 | 6/2016 | Anderson et al. |
| 2023/0065079 | A1 | 3/2023 | Murakami et al. |

FOREIGN PATENT DOCUMENTS

| | | |
|---|---|---|
| CN | 1528743 A | 9/2004 |
| CN | 102421454 A | 4/2012 |
| CN | 105523977 A | 4/2016 |
| WO | WO-2000/63216 A1 | 10/2000 |
| WO | 2014/179341 A1 | 11/2014 |
| WO | 2020/017620 A1 | 1/2020 |

OTHER PUBLICATIONS

Chinese Office Action for Application No. 202180009363.X, dated Aug. 16, 2023, 13 pages.
International Search Report and Written Opinion for Application No. PCT/JP2021/001154, dated Mar. 2, 2021, 8 pages.
U.S. Appl. No. 17/793,091, filed Jul. 15, 2022, Pending.
Chinese Office Action for Application No. 201980048149.8, dated Jul. 22, 2022, 13 pages.
European Office Action for Application No. 19837826.7, dated Mar. 31, 2022, 13 pages.
U.S. Appl. No. 17/793,091, filed Jul. 15, 2022, Published.
Degrado et al., Synthesis and preliminary evaluation of (18)F-labeled 4-thia palmitate as a PET tracer of myocardial fatty acid oxidation. Nucl Med Biol. Apr. 2000;27(3):221-31.
Indian Office Action for Application No. 202147002416, dated Oct. 19, 2022, 7 pages.
Cai et al., Synthesis and preliminary evaluation of an $^{18}$F-labeled oleic acid analog for PET imaging of fatty acid uptake and metabolism. Nucl Med Biol. Jan. 2016;43(1):108-115.
Degrado et al., Synthesis and preliminary evaluation of 18-(18)F-fluoro-4-thia-oleate as a PET probe of fatty acid oxidation. J Nucl Med. Aug. 2010;51(8):1310-7.
Nishimura et al., Fatty acid myocardial imaging using 123I-beta-methyl-iodophenyl pentadecanoic acid (BMIPP): comparison of myocardial perfusion and fatty acid utilization in canine myocardial infarction (occlusion and reperfusion model). Eur J Nucl Med. 1989;15(7):341-5.
Pandey et al., Structure dependence of long-chain [18F]fluorothia fatty acids as myocardial fatty acid oxidation probes. J Med Chem. Dec. 13, 2012;55(23):10674-84.
International Search Report and Written Opinion for Application No. PCT/JP2019/028380, dated Oct. 8, 2019, 12 pages.
Chinese Office Action for Application No. 201980048149.8, dated Feb. 16, 2023, 7 pages.
U.S. Appl. No. 17/793,091, filed Jul. 15, 2022, U.S. Pub. No. 2023-0065079, Published.
European Association of Nuclear Medicine Oct. 22 - 30, 2020 Virtual. Eur J Nucl Med Mol Imaging. Sep. 2020;47 (Suppl 1):1-753.
European Office Action for Application No. 21740758.4, dated Feb. 27, 2024, 14 pages.

*Primary Examiner* — Jake M Vu
(74) *Attorney, Agent, or Firm* — McCarter & English, LLP; Wei Song; James M. Alburger

(57) ABSTRACT

Provided is a labeled fatty acid derivative for diagnostic imaging that enables quantification of fatty acid metabolic activity in the heart muscle.
[Means for Solution]
The present inventors have conducted intensive investigations on a method that enables quantification of fatty acid metabolic activity and thus have found that a labeled fatty acid derivative typified by 3-{[(5Z)-3-[$^{18}$F]fluorotetradeca-5-en-1-yl]sulfanyl}propanoic acid or a salt thereof has excellent accumulation to the heart muscle and thus enables imaging of fatty acid metabolic activity by positron emission tomography (PET). Therefore, the labeled fatty acid derivative of the present invention can be used as a radiolabeled tracer for rapid and non-invasive quantification of fatty acid metabolic activity in the heart muscle, diagnostic imaging of heart disease typified by an ischemic heart disease, diagnostic imaging of the therapeutic effect of a therapeutic drug for heart disease, and the like.

14 Claims, 2 Drawing Sheets

(A)

(B)

(C)

(D)

(A) MIP (B) MIP (A)

(B)

FATTY ACID DERIVATIVE LABELED WITH POSITRON-EMITTING RADIONUCLIDE

RELATED APPLICATIONS

This application is a 371 U.S. national stage filing, under 35 U.S.C. § 371(c), of International Application No. PCT/JP2019/028380, filed Jul. 19, 2019, which claims priority to Japanese Patent Application No. 2018-136483, filed Jul. 20, 2018.

TECHNICAL FIELD

The present invention relates to a fatty acid derivative labeled with a positron-emitting radionuclide or a salt thereof. Further, the present invention relates to a composition for diagnostic imaging containing the labeled fatty acid derivative or a salt thereof, and a kit for preparing the same.

BACKGROUND ART

The heart requires a large amount of adenosine triphosphate (ATP) to pump blood throughout the body, most of which is produced by oxidative metabolism in mitochondria. Various substrates such as fatty acids, glucose, and the like are metabolized in the heart muscle, but in a state in which oxygen is distributed to the heart muscle, about 60% to 90% of the required ATP is produced by β-oxidation of fatty acids. On the other hand, it has been found that in an ischemic state, the rate of oxidative metabolism decreases and the rate of ATP production by anaerobic metabolism increases (Expert Rev. Cardiovasc. Ther. 2007; 5 (6): 1123-1134). Therefore, the quantification of fatty acid metabolic activity in the heart muscle is one of the effective means for diagnosing heart disease.

This quantification of fatty acid metabolic activity is carried out by positron emission tomography (PET) or single photon emission computed tomography (SPECT) using a labeled long-chain fatty acid derivative as a radiolabeled tracer. As a radiolabeled tracer used for SPECT, 15-(p-[$^{123}$I]iodophenyl)-3(R,S)-methylpentadecanoic acid (hereinafter, abbreviated as [$^{123}$I]BMIPP) represented by the following formula has been reported (Non-Patent Document 1), and has been actually used in clinical practice for diagnosing heart disease.

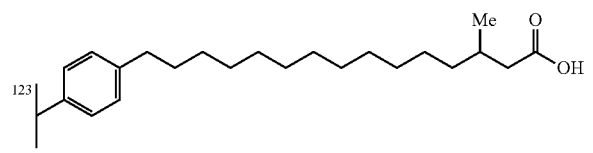 [SMILES: CC(CCCCCCCCCCCCc1ccc(C(C)C)cc1)CC(=O)O]

(In the formula, Me represents a methyl group. The same shall apply hereinafter.)

On the other hand, as a radiolabeled tracer used for PET, 16-[$^{18}$F]fluoro-4-thiahexadecanoic acid represented by the following formula (also referred to as 16-[$^{18}$F]fluoro-4-thiapalmitic acid; hereinafter, abbreviated as [$^{18}$F]FTP) has been known (Patent Document 1).

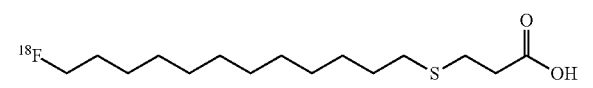 [SMILES: O=C(O)CCSCCCCCCCCCCCC[18F]]

Similarly, as the radiolabeled tracer used for PET, 3-{[(5Z)-14-[$^{18}$F]fluorotetradeca-5-en-1-yl]sulfanyl}propanoic acid represented by the following formula, which has improved accumulation in the heart compared to the [$^{18}$F]FTP, (also referred to as 18-[$^{18}$F]fluoro-4-thiaoleic acid; hereinafter, abbreviated as [$^{18}$F]FTO) has been reported (Non-Patent Document 2).

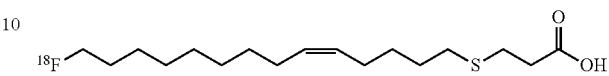

However, [$^{123}$I]BMIPP used as a tracer for diagnostic imaging by SPECT has a problem of low sensitivity and resolution, and although [$^{18}$F]FTP and [$^{18}$F]FTO as the tracer used for diagnostic imaging by PET are superior in SPECT using the [$^{123}$I]BMIPP, further improvement in sensitivity and resolution is required for more accurate diagnosis.

RELATED ART

Patent Document

[Patent Document 1] International Publication No. 2000/063216

Non-Patent Document

[Non-Patent Document 1] Eur. J. Nucl. Med., 1989, 15, 341-345

[Non-Patent Document 2] J. Nucl. Med., 2010, 51(8), 1310-1317

DISCLOSURE OF INVENTION

Problems to be Solved by the Invention

There is a strong desire for the development of a radiolabeled tracer that has selective accumulation to the heart and improved sensitivity and resolution and enables accurate diagnosis of heart disease.

Means for Solving the Problems

In PET images using [$^{18}$F]FTO which is a known PET tracer, accumulation of [$^{18}$F]fluorine is confirmed not only in the heart but also in the bone. Thus, it is considered that the background value is increased and the sensitivity and resolution are decreased (for example, refer to PET images with [$^{18}$F]FTO in FIGS. 1 and 2). Therefore, in order to find a labeled fatty acid derivative in which the accumulation of [$^{18}$F]fluorine in the bone was reduced, 3-{[(5Z)-11-[$^{18}$F]fluorotetradeca-5-en-1-yl]sulfanyl}propanoic acid (also referred to as 15-[$^{18}$F]fluoro-4-thiaoleic acid; hereinafter, abbreviated as 15-[$^{18}$F]FTO) and 3-{[(5Z)-13-[$^{18}$F]fluorotetradeca-5-en-1-yl]sulfanyl}propanoic acid (also referred to as 17-[$^{18}$F]fluoro-4-thiaoleic acid; hereinafter, abbreviated as 17-[$^{18}$F]FTO) in which the substitution position of [$^{18}$F]fluorine was changed, described in Reference Examples 5 and 6 below, were produced to conduct an investigation. However, similarly, the accumulation in the bone was also observed (refer to Table 6).

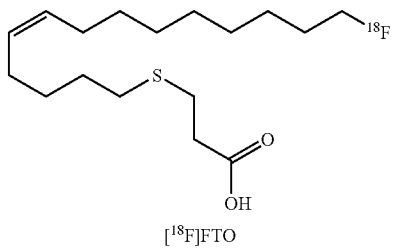

[¹⁸F]FTO

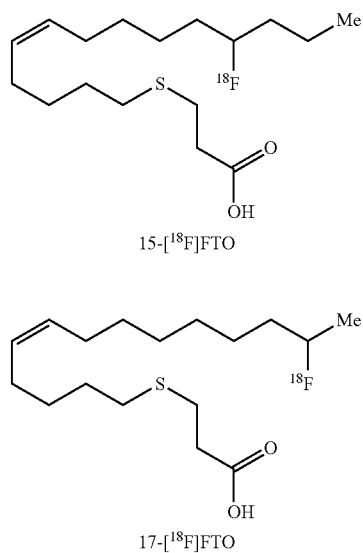

15-[¹⁸F]FTO

17-[¹⁸F]FTO

In further investigations, β-oxidation and ω-oxidation are present in the oxidative metabolism pathway of long-chain fatty acids. In the ω-oxidation, fatty acids are metabolized from the terminal side away from the carboxyl group to generate [¹⁸F]fluoride ions in the process of metabolism, and [¹⁸F]sodium fluoride has accumulation to the bone. Therefore, it is assumed that the [¹⁸F]fluoride ions generated in the process of metabolism of [¹⁸F]FTO may be the cause of non-specific accumulation to the bone.

As a result of conducting intensive investigations for the purpose of producing a labeled fatty acid derivative that is less likely to generate [¹⁸F]fluoride ions by metabolism, the present inventors and the like have found that unexpectedly, a labeled fatty acid derivative represented by the formula (I) in which [¹⁸F]fluorine is substituted on the carbon atom between the sulfur atom and the double bond of 3-{[(5Z)-tetradeca-5-en-1-yl]sulfanyl}propanoic acid can be used as a radiolabeled tracer which has low accumulation of [¹⁸F] fluorine to the bone compared to the conventional [¹⁸F]FTO, is selectively accumulated in the heart, and enables imaging of fatty acid metabolism in the heart muscle with high sensitivity, and thus have completed the present invention. It is presumed that by introducing [¹⁸F]fluorine into a specific substitution position, the metabolic stability against ω-oxidation from the terminal side away from the carboxyl group is improved, the generation of [¹⁸F]fluoride ions is suppressed, and as a result, the accumulation in the bone is reduced.

That is, the present invention relates to a labeled fatty acid derivative represented by the formula (I) or a salt thereof.

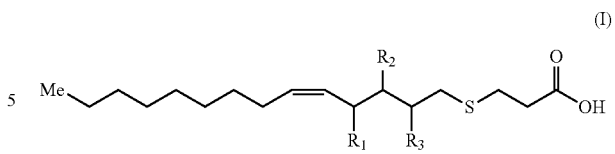

(In the formula, any one of $R_1$ to $R_3$ is ¹⁸F, and the other two are H.)

Unless otherwise specified, in a case where a symbol in a chemical formula in the specification is also used in another chemical formula, the same symbol has the same meaning.

In addition, the present invention relates to (1) a labeled fatty acid derivative represented by formula (I) or a salt thereof, and a composition for diagnostic imaging containing a pharmaceutically acceptable carrier, particularly a composition for diagnostic imaging of heart disease, (2) use of the labeled fatty acid derivative represented by the formula (I) or a salt thereof for the manufacture of a composition for diagnostic imaging of heart disease, (3) use of the labeled fatty acid derivative represented by the formula (I) or a salt thereof for diagnostic imaging of heart disease, (4) a labeled fatty acid derivative represented by the formula (I) or a salt thereof for use in diagnostic imaging of heart disease, (5) a method for diagnostic imaging of heart disease including administering a detectable amount of the labeled fatty acid derivative represented by the formula (I) or a salt thereof to a subject, (6) an intermediate compound, which can be converted into the labeled fatty acid derivative represented by the formula (I) or a salt thereof, or a salt thereof, (7) a method for producing the labeled fatty acid derivative represented by the formula (I) or a salt thereof from the intermediate compound or a salt thereof according to (6), and (8) a kit for preparing the composition for diagnostic imaging according to (1) including the intermediate compound or a salt thereof according to (6).

Effects of the Invention

The labeled fatty acid derivative represented by the formula (I) according to the present invention or a salt thereof does not cause an increase in background value due to accumulation in the bone compared to [¹⁸F]FTO which is a known labeled fatty acid, has excellent accumulation to the heart muscle and enables imaging of fatty acid metabolic activity by PET. Therefore, the labeled fatty acid derivative represented by the formula (I) according to the present invention or a salt thereof can be used as a radiolabeled tracer for sorting heart disease patients, diagnostic imaging of the therapeutic effect of a therapeutic drug for heart disease, and the like.

EMBODIMENTS FOR CARRYING OUT THE INVENTION

Figure 1:
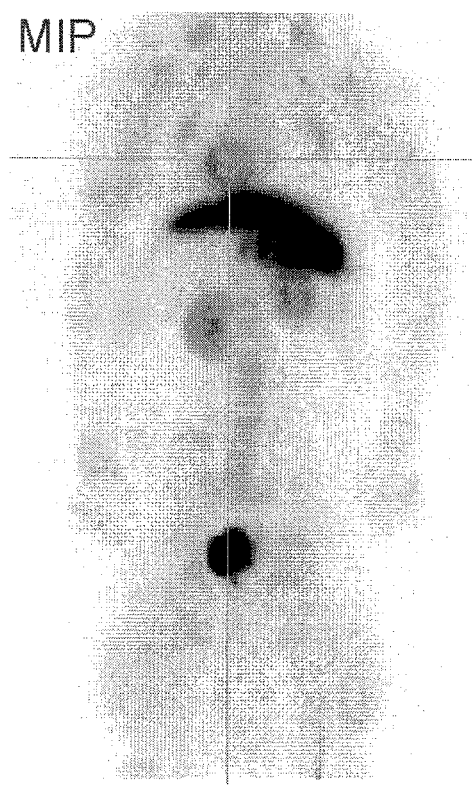
FIG. 1 shows PET images in which a compound ([¹⁸F] FTO) of Reference Example 4 and a compound (7-[¹⁸F] FTO) of Example 1 are administered to normal cynomolgus monkeys in Example 5, respectively. PET images 60 minutes and 240 minutes after administration of [¹⁸F]FTO are shown in (A) and (B), respectively. In addition, PET images 60 minutes and 240 minutes after administration of 7-[$^{18}$F] FTO are shown in (C) and (D), respectively.
Figure 1:
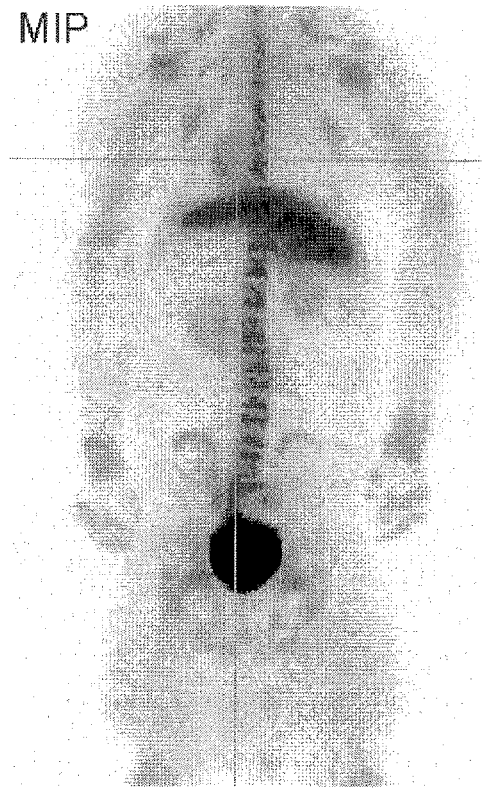
Figure 1:
Figure 1:
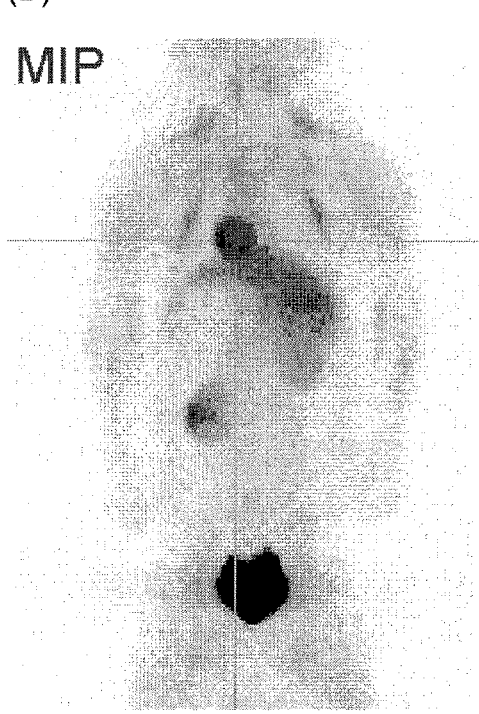

Hereinafter, the present invention will be described in detail.

An embodiment of a labeled fatty acid derivative represented by the formula (I) according to the present invention or a salt thereof is a labeled fatty acid derivative in which $R_1$ is H, or a salt thereof.

An embodiment of the labeled fatty acid derivative represented by the formula (I) of the present invention or a salt thereof is a labeled fatty acid derivative selected from the following group or a salt thereof.

(1) A compound in which $R_1$ is $^{18}$F and $R_2$ and $R_3$ are H, that is, 3-{[(5Z)-4-[$^{18}$F]fluorotetradeca-5-en-1-yl] sulfanyl}propanoic acid (also referred to as 8-[$^{18}$F] fluoro-4-thiaoleic acid; hereinafter, abbreviated as 8-[$^{18}$F]FTO)

(2) A compound in which $R_2$ is $^{18}$F and $R_1$ and $R_3$ are H, that is, 3-{[(5Z)-3-[$^{18}$F]fluorotetradeca-5-en-1-yl] sulfanyl}propanoic acid (also referred to as 7-[$^{18}$F] fluoro-4-thiaoleic acid; hereinafter, abbreviated as 7-[$^{18}$F]FTO)

(3) A Compound in which $R_3$ is $^{18}$F and $R_1$ and $R_2$ are H, that is, 3-{[(5Z)-2-[$^{18}$F]fluorotetradeca-5-en-1-yl] sulfanyl}propanoic acid (also referred to as 6-[$^{18}$F] fluoro-4-thiaoleic acid; hereinafter, abbreviated as 6-[$^{18}$F]FTO)

The labeled fatty acid derivative represented by the formula (I) of the present invention or a salt thereof is used as a radiolabeled tracer for diagnostic imaging such as, PET and the like. The labeled fatty acid derivative of the present invention has accumulation in the heart muscle in a biological body, enables imaging of fatty acid metabolic activity by PET and a similar imaging method, and is used for diagnostic imaging of heart disease, particularly, ischemic heart disease. In small animal tests, as in vivo diagnostic imaging means, a planar positron imaging system (PPIS) which a device that acquires planar accumulated images instead of tomographic images can be used in addition to a PET system for small animals. Further, the labeled fatty acid derivative can be used for autoradiography, which is image analysis means for a sections of extracted organs, and for evaluation of accumulation in extracted organs using a gamma counter.

The positron-emitting radionuclide used in the labeled fatty acid derivative of the present invention is $^{18}$F.

Generally, $^{18}$F is produced by a device called a cyclotron. The $^{18}$F produced can be used to label the compound represented by the formula (I). A desired nuclide is obtained from a (ultra) small cyclotron installed in a facility to be used, the labeled fatty acid derivative represented by the formula (I) of the present invention or a salt thereof is produced by a method known in the art, and thus a composition for diagnostic imaging can be prepared.

The labeled fatty acid derivative represented by the formula (I) of the present invention or a salt thereof may have an asymmetric center, and an enantiomer (optical isomer) based on the asymmetric center may be present. The compound represented by the formula (I) or a salt thereof includes any of isolated individual enantiomers such as an (R) body and an (S) body, and mixtures thereof (including a racemic mixture or a non-racemic mixture).

In addition, the labeled fatty acid derivative represented by the formula (I) of the present invention may form salts depending on conditions, and these salts are also included in the present invention. Here, examples of the salts include salts with inorganic bases such as sodium, potassium, magnesium, calcium, aluminum, and the like, salts with organic bases such as methylamine, ethylamine, ethanolamine, lysine, ornithine, and the like, salts with various amino acids and amino acid derivatives such as acetyl leucine, ammonium salts, and the like.

Further, the labeled fatty acid derivative represented by the formula (I) of the present invention or a salt thereof may be provided as a hydrate, a solvate, or a crystal polymorphic substance, and the present invention includes these forms.

The present invention includes an intermediate compound, which can be converted into the labeled fatty acid derivative represented by the formula (I) or a salt thereof, or a salt thereof. Examples of the "intermediate compound which can be converted into the labeled fatty acid derivative represented by the formula (I) or a salt thereof" include a compound represented by the formula (1i). Another embodiment includes a compound represented by the formula (1h), which is a precursor of the compound represented by the formula (1i).

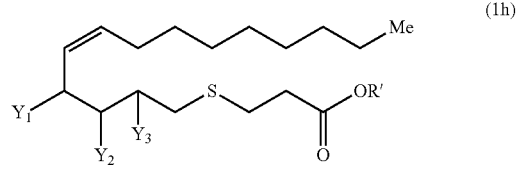

(1h)

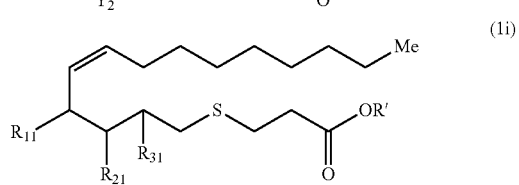

(1i)

(In the formula, any one of $Y_1$ to $Y_3$ is OH, and the other two are H. Any one of $R_{11}$ to $R_{31}$ is a leaving group, and the other two are H. In addition, R' is H or a lower alkyl group which may be substituted. The same shall apply hereinafter.)

The present invention also includes a method for producing the labeled fatty acid derivative represented by the formula (I) or a salt thereof including a step of allowing a [$^{18}$F]fluoride ion to react with the intermediate compound, which can be converted into the labeled fatty acid derivative represented by the formula (I) or a salt thereof, or a salt thereof.

Further, the present invention includes at least a kit for preparing a composition for diagnostic imaging containing the intermediate compound, which can be converted into the labeled fatty acid derivative represented by formula (I) or a salt thereof, or a salt thereof. An embodiment of the kit of the present invention is a kit for rapid synthesis of the labeled fatty acid derivative of the present invention. The kit includes a kit for preparing a composition for diagnostic imaging containing the intermediate compound, which can be converted into the labeled fatty acid derivative represented by the formula (I) or a salt thereof, or a salt thereof, and a reagent for labeling $^{18}$F, and is a kit containing other reagents, solvents, and the like if desired. The kit can be used for preparing the composition for diagnostic imaging of the present invention as required. The kit can also include instruments such as a reaction vessel, a device for transferring isotopic material to the reaction vessel, a pre-packed separation column for separating a product from excess reactants, a shield, and the like as known in the art.

In the specification, the "reagent for labeling $^{18}$F" is a reagent containing [$^{18}$F]fluoride ions, and examples thereof include [$^{18}$F]TBAF, [$^{18}$F]KF, and the like.

In the specification, the expression "may be substituted" means "unsubstituted" or one or more arbitrary substituents to bind thereto.

The "lower alkyl" is a linear or branched alkyl having 1 to 6 carbon atoms (hereinafter, also referred to as $C_{1-6}$), and examples thereof include methyl, ethyl, n-propyl, isopropyl, n-butyl, isobutyl, s-butyl, t-butyl, n-pentyl, n-hexyl, and the like. As one embodiment, the lower alkyl is $C_{1-4}$ alkyl, as another embodiment, methyl, ethyl or t-butyl, and as still another embodiment, methyl.

The "leaving group" means a substituent that is eliminated by a nucleophilic substitution reaction, and examples thereof include a sulfonyl group and halogen. However, there is no limitation thereto. Examples of the sulfonyl group include a p-toluenesulfonyloxy group, a p-nitrobenzenesulfonyloxy group, a methanesulfonyloxy group, a trifluoromethanesulfonyloxy group and the like, and as one embodiment, the sulfonyl group is a p-toluenesulfonyloxy group or a p-nitrobenzenesulfonyloxy group. Examples of the halogen include Cl, Br, I, and the like, and as one embodiment, the halogen is Br.

Specific embodiments of the present invention include the following.

(1-1) A labeled fatty acid derivative represented by the formula (I) or a salt thereof.
(1-2) The labeled fatty acid derivative or a salt thereof according to (1-1), in which $R_1$ is H.
(1-3) 7-[$^{18}$F]FTO or a salt thereof.
(1-4) 6-[$^{18}$F]FTO or a salt thereof.
(2) A composition for diagnostic imaging including the labeled fatty acid derivative or a salt thereof according to any one of (1-1) to (1-4), and a pharmaceutically acceptable carrier.
(3) The composition for diagnostic imaging according to (2), which is a composition for diagnostic imaging of heart disease.
(4) The composition for diagnostic imaging according to (3), in which the heart disease is an ischemic heart disease.
(5) Use of the labeled fatty acid derivative or a salt thereof according to any one of (1-1) to (1-4) for the manufacture of a composition for diagnostic imaging of heart disease.
(6) The use of the labeled fatty acid derivative or a salt thereof according to (5), in which the heart disease is an ischemic heart disease.
(7) Use of the labeled fatty acid derivative or a salt thereof according to any one of (1-1) to (1-4) for diagnostic imaging of heart disease.
(8) The use of the labeled fatty acid derivative or a salt thereof according to (7), in which the heart disease is an ischemic heart disease.
(9) The labeled fatty acid derivative or salt thereof according to any one of (1-1) to (1-4) for use in diagnostic imaging of heart disease.
(10) The labeled fatty acid derivative or salt thereof according to (9), in which the heart disease is an ischemic heart disease.
(11) A method for diagnostic imaging of heart disease including administering a detectable amount of the labeled fatty acid derivative or a salt thereof according to any one of (1-1) to (1-4) to a subject.
(12) The method for diagnostic imaging according to (11), in which the heart disease is an ischemic heart disease.
(13-1) A compound represented by formula (1i) or a salt thereof.
(13-2) The compound or a salt thereof according to (13-1), in which R' is a lower alkyl group.
(13-3) The compound or a salt thereof according to (13-2), in which the lower alkyl group is methyl, ethyl, or t-butyl.
(13-4) The compound or a salt thereof according to (13-2), in which the lower alkyl group is methyl.
(13-5) The compound or a salt thereof according to any one of (13-1) to (13-4), in which $R_{21}$ is a leaving group and $R_{11}$ and $R_{31}$ are H.
(13-6) The compound or a salt thereof according to any one of (13-2) to (13-5), in which the leaving group is a p-toluenesulfonyloxy group, a p-nitrobenzenesulfonyloxy group, or a bromo group.
(13-7) The compound or a salt thereof according to any one of (13-2) to (13-5), in which the leaving group is a p-toluenesulfonyloxy group.
(13-8) The compound or a salt thereof according to any one of (13-2) to (13-5), in which the leaving group is a p-nitrobenzenesulfonyloxy group.
(13-9) The compound or a salt thereof according to any one of (13-2) to (13-5), in which the leaving group is a bromo group.
(14) A method for producing the labeled fatty acid derivative or a salt thereof according to any one of (1-1) to (1-4) including a step of allowing a [$^{18}$F]fluoride ion to react with the compound or a salt thereof according to any one of (13-1) to (13-9).
(15) A kit for preparing the composition for diagnostic imaging according to any one of (2) to (4) including the compound or a salt thereof according to any one of (13-1) to (13-9).

(Production Method)

The labeled fatty acid derivative represented by the formula (I) or a salt thereof can be produced by applying various known synthetic methods using its basic structure or properties based on the type of substituent. At that time, depending on the type of functional group, in terms of production technology, it is effective to replace the functional group with an appropriate protective group (a group that can be easily converted to the functional group) at the stage from the starting material to the intermediate in some cases. Examples of such protective groups include the protective groups described in "Greene's Protective Groups in Organic Synthesis (5th Edition, 2014)" by P. G. M. Wuts, and the like, and depending on the reaction conditions thereof, the protective group may be appropriately selected and used. In such a method, a desired compound can be obtained by introducing the protective group to carry out the reaction, and then removing the protective group as required.

Hereinafter, a typical method for producing the labeled fatty acid derivative represented by the formula (I) or a salt thereof will be described. Each production method can also be carried out with reference to the references attached to the description. The production method of the present invention is not limited to the examples shown below.

In addition, the following abbreviations may be used in the specification.

AlkylFluor (trademark)=1,3-bis(2,6-diisopropylphenyl)-2-fluoroimidazolium tetrafluoroborate, DBU=1,8-diazabicyclo[5.4.0]-7-undecene, EtOAc=ethyl acetate, HMPA=hexamethylphosphoric acid triamide, MeCN=acetonitrile, MeOH=methanol, Nos=p-nitrobenzenesulfonyl, Ph=phenyl, TBAF=tetra-n-butylammonium fluoride, TBDMS=t-butyldimethylsilyl, TBDPS=t-butyldiphenylsilyl, TFA=trifluoroacetic acid, THF=tetrahydrofuran, THP=tetrahydropyran-2-yl, Ts=p-toluenesulfonyl.

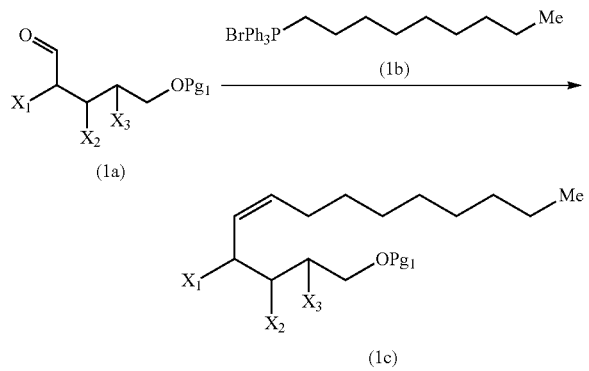

(In the formula, any one of $X_1$, $X_2$, and $X_3$ is $OPg_2$, and the other two are H. Here, $Pg_1$ and $Pg_2$ each represent a protective group. Examples of the protective group include TBDMS, TBDPS, trimethylsilyl, triethylsilyl, triisopropylsilyl, methoxymethyl, 1-ethoxyethyl, [2-(trimethylsilyl)ethoxy]methyl, THP, and p-methoxybenzyl, and as one embodiment, the protective group is TBDMS, TBDPS, or THP. The same shall apply hereinafter.)

Compound (1c) can be produced from compound (1a) and compound (1b).

The reaction is carried out by performing stirring in a solvent inert to the reaction in the presence of a base at −78° C. to room temperature usually for 0.1 hours to 3 days. Here, examples of the solvent include THF, 1,4-dioxane, HMPA, and the like, and a mixture thereof. Examples of the base include potassium hexamethyldisilazide, potassium-t-butoxide, and the like.

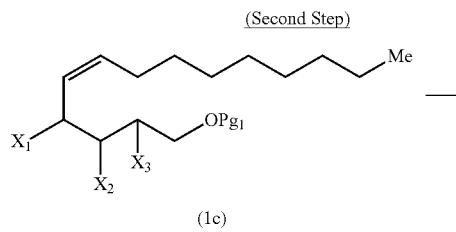

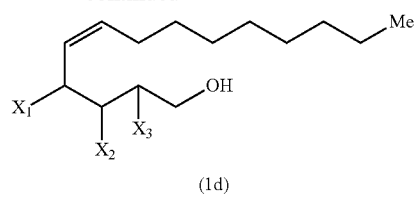

Compound (1d) can be produced by deprotecting a protective group $Pg_1$ of compound (1c). Deprotection can be carried out using a method well known to those of skill in the art, and for example, deprotection can be carried out by performing stirring in a solvent inert to the reaction in the presence of a fluorine reagent or acid at −78° C. to room temperature usually for 0.1 hours to 3 days. Examples of the fluorine reagent include TBAF, pyridine hydrofluoric acid, and the like, and acetic acid may be added at this time. Examples of the acid include hydrochloric acid, p-toluenesulfonic acid, and the like.

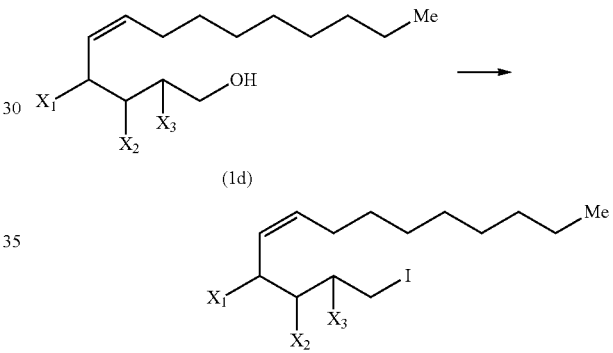

Compound (1e) can be produced by converting the hydroxyl group of compound (1d) into iodine by an iodination reaction.

The iodination reaction is carried out by stirring compound (1d) and iodine in a solvent inert to the reaction in the presence of triphenylphosphine and a base at room temperature under ice cooling usually for 0.1 hours to 3 days. Here, examples of the base include imidazole, trimethylamine, and the like. Examples of the solvent include dichloromethane, THF, and the like.

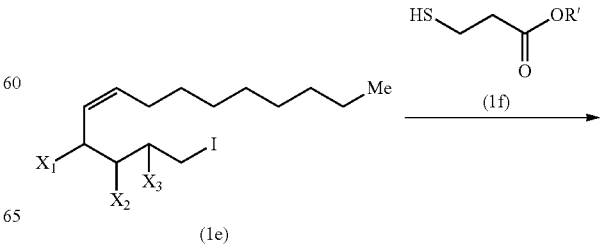

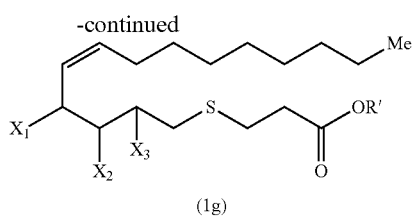

(1g)

(In the formula, R' represents H or a lower alkyl group which may be substituted. The same shall apply hereinafter.)

Compound (1g) can be produced from compound (1e) and compound (1f).

The reaction is carried out by performing stirring compound (1e) and compound (1f) in a solvent inert to the reaction in the presence of a base at ice cooling to room temperature usually for 0.1 hours to 3 days. Here, examples of the solvent include THF, 1,4-dioxane, and the like. Examples of the base include sodium hydride, potassium-t-butoxide, and the like.

(Fifth Step)

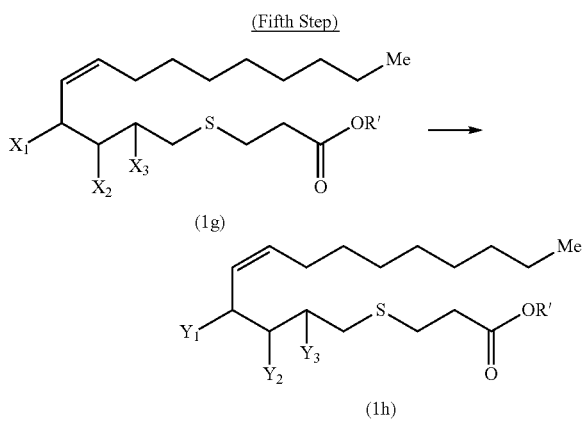

(In the formula, when $X_1$ is $OPg_2$, $Y_1$ is OH, and when $X_1$ is H, $Y_1$ is H. When $X_2$ is $OPg_2$, $Y_2$ is OH, and when $X_2$ is H, $Y_2$ is H. When $X_3$ is $OPg_2$, $Y_3$ is OH, and when $X_3$ is H, $Y_3$ is H. The same shall apply hereinafter.)

Compound (1h) can be produced by deprotecting a protective group $Pg_2$ of compound (1g). Deprotection can be carried out in the same manner as in the second step.

(Sixth Step)

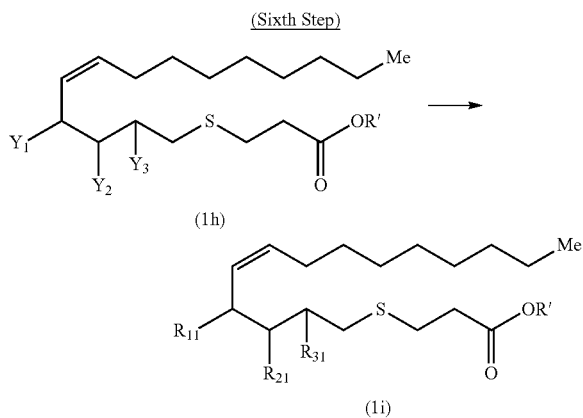

(In the formula, when $Y_1$ is OH, $R_{11}$ is a leaving group, and when $Y_1$ is H, $R_{11}$ is H. When $Y_2$ is OH, $R_{21}$ is a leaving group, and when $Y_2$ is H, $R_{21}$ is H. When $Y_3$ is OH, $R_{31}$ is a leaving group, and when $Y_3$ is H, $R_{31}$ is H.)

Compound (1i) can be produced by converting the hydroxyl group of compound (1h) into a leaving group.

When the leaving group is a sulfonyl group, in the reaction, compound (1h) and a sulfonylating agent are stirred in a solvent inert to the reaction in the presence of a base at ice cooling to room temperature usually for 0.1 hours to 3 days. Examples of the sulfonylating agent include chloride (p-toluenesulfonyl), chloride (p-nitrobenzenesulfonyl), chloride (methanesulfonyl), trifluoromethanesulfonic anhydride, and the like. Examples of the solvent include dichloromethane, THF, and the like. Examples of the base include triethylamine, diisopropylethylamine, and the like. At this time, trimethylamine hydrochloride may be added.

In addition, when the leaving group is halogen, in the reaction, compound (1h) and a halogenating agent are stirred in a solvent inert to the reaction in the presence of triphenylphosphine at ice cooling to room temperature usually for 0.1 hours to 3 hours. Here, examples of the halogenating agent include carbon tetrabromide, iodine, and the like. Examples of the solvent include carbon tetrachloride, dichloromethane, THF, and the like. At this time, a base such as imidazole, trimethylamine, or the like may be added.

(Seventh Step)

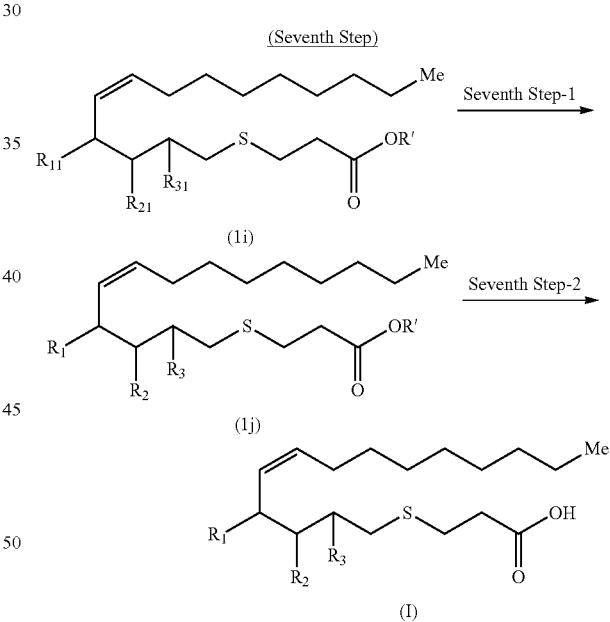

(In the formula, when $R_{11}$ is a leaving group, $R_1$ is $^{18}F$, and when $R_{11}$ is H, $R_1$ is H. When $R_{21}$ is a leaving group, $R_2$ is $^{18}F$, and when $R_{21}$ is H, $R_2$ is H. When $R_{31}$ is a leaving group, $R_3$ is $^{18}F$, and when $R_{31}$ is H, $R_3$ is H.)

(Seventh Step-1)

Compound (1j) can be produced by, for example, causing a reaction of compound (1i) and a [$^{18}F$]fluoride ion aqueous solution, [$^{18}F$]tetra-n-butylammonium fluoride ([$^{18}F$] TBAF), [$^{18}F$]KF, or the like, which is a reagent containing a positron-emitting radionuclide $^{18}F$ produced by a cyclotron by a method well known to those skilled in the art, under heating.

(Seventh Step-2)

Compound (I) can be produced from compound (1j) by a method well known to those skilled in the art, and can be produced by, for example, performing stirring in a solvent inert to the reaction in the presence of an aqueous base solution at ice cooling to 110° C. usually for 0.1 hours to 3 days. Examples of the base include sodium hydroxide, potassium hydroxide, and the like. When R' is H, the seventh step-2 is omitted.

The isolation and purification of the compound represented by the formula (I) or a salt thereof produced in this manner are performed by applying ordinary chemical operations such as extraction, concentration, evaporation, crystallization, filtration, recrystallization, various types of chromatography, and the like.

Various isomers can be produced by selecting an appropriate starting compound, or can be separated by using a difference in physicochemical properties between the isomers. For example, optical isomers can be obtained by a general optical resolution method of a racemic body (for example, fractional crystallization leading to a diastereomeric salt with an optically active base or acid, chromatography using a chiral column and the like, and the like), and can be produced from an appropriate optically active starting compound.

A composition for diagnostic imaging according to the present invention can be produced by combining the labeled fatty acid derivative with at least one pharmaceutically acceptable carrier. The composition for diagnostic imaging of the present invention preferably has a dosage form suitable for intravenous administration, and is, for example, an injection for intravenous administration. Examples of the injection include those containing a sterile aqueous or non-aqueous solution, suspension, and emulsion. As the aqueous solvent, for example, distilled water for injection or physiological saline is included. Examples of the non-aqueous solvent include propylene glycol, polyethylene glycol, vegetable oils such as olive oil, alcohols such as ethanol, Polysorbate 80 (trade name), and the like. Such a composition may further contain a tonicity agent, a preservative, a wetting agent, an emulsifying agent, a dispersing agent, a stabilizing agent, or a solubilizing agent. These are sterilized by, for example, filtering in which these are filtered through a bacteria retentive filter, by being mixed with a germicide, or by irradiation. In addition, these can be used by being prepared as a sterile solid composition and dissolved or suspended in sterile water or a sterile solvent for injection before use. As one embodiment, the composition for diagnostic imaging of the present invention is an injection for intravenous administration. As another embodiment, the composition is an aqueous solution.

The composition for diagnostic imaging of the present invention can be used by adjusting the dose according to the imaging method (such as PET and the like) used, the type of disease, the age and state of the patient, the examination site, and the purpose of imaging. Although the composition for diagnostic imaging of the present invention is required to contain a detectable amount of the labeled fatty acid derivative, it is required to pay sufficient attention to the exposure dose of the patient. For example, the amount of the radioactivity of the composition for diagnostic imaging of the present invention labeled with $^{18}$F is about 1.85 to 740 megabecquerels (MBq), as one embodiment, the radioactivity is about 1.85 to 37 MBq, and as another embodiment, the radioactivity is about 37 to 740 MBq. The composition is administered once or in multiple time in a divided manner, or persistently instilled.

EXAMPLES

Hereinafter, a method for producing the labeled fatty acid derivative of the present invention and the effect thereof will be described in more detail based on examples. The present invention is not limited to the compounds described in the following examples.

In addition, the following abbreviations may be used in Examples, Reference Examples and Tables below in some cases.

The following abbreviations represent the followings, respectively: Ex: Example number (The branch number indicates the step number in which the compound is obtained as a result in the example. For example, the compound whose Example number is Ex1-3 means that the compound is a compound obtained in the third step of Example 1), Ref: Reference example number, Str: Chemical structural formula, DAT: Physicochemical data, ESI+: m/z value in mass spectrometry (Ionization method ESI, representing [M+H]$^+$ unless otherwise specified), ESI−: m/z value in mass spectrometry (Ionization method ESI, representing [M−H]$^-$ unless otherwise specified), APCI/ESI+ (Ionization methods APCI and ESI are performed at the same time, representing [M+H]$^+$ unless otherwise specified), CI+: m/z value in mass spectrometry (Ionization method CI, representing [M+H]$^+$ unless otherwise specified), NMR: δ value (ppm) of signal in 1H-NMR in CDCl$_3$, J: coupling constant, s: singlet, d: doublet, t: triplet, m: multiplet, and Ci: Curie, the unit of radioactivity (1 Ci=3.7×10$^{10}$ Bq).

For convenience, the concentration mol/L is represented by M. For example, a 1 M aqueous sodium hydroxide solution means a 1 mol/L aqueous sodium hydroxide solution.

Example 1

First step: Nonyltriphenylphosphonium bromide (7.39 g) was dissolved in a mixture of THF (190 mL) and HMPA (7.4 mL) under a nitrogen gas stream and the mixture was cooled to −78° C. After potassium hexamethyldisilazide (1 M THF solution, 15.7 mL) was added dropwise, the mixture was stirred under ice cooling for 1 hour. After cooling the reaction liquid to −78° C., a THF (10 mL) solution of 5-{[t-butyl(dimethyl)silyl]oxy}-3-{[t-butyl(diphenyl)silyl]oxy}pentanal (2.47 g) was added dropwise and the mixture was stirred at the same temperature for 3 hours. After stirring the mixture at room temperature for 14 hours, water was added. Ethyl acetate and water were added, and the organic layer was separated, washed with saturated brine, then dried over magnesium sulfate, and concentrated under reduced pressure. The residue was purified by silica gel column chromatography (EtOAc/n-hexane) to obtain 2,2,9,9,10,10-hexamethyl-3,3-diphenyl-5-[(2Z)-undeca-2-en-1-yl]-4,8-dioxa-3,9-disilaundecane (2.93 g) as an oily substance.

Second step: 2,2,9,9,10,10-hexamethyl-3,3-diphenyl-5-[(2Z)-undeca-2-en-1-yl]-4,8-dioxa-3,9-disilaundecane (2.94 g) was dissolved in a mixture of THF (30 mL) and water (1.5 mL), p-toluenesulfonic acid monohydrate (96 mg) was added at room temperature, and the mixture was stirred at the same temperature for 20 hours. Aqueous sodium bicarbonate and ethyl acetate were added, and the organic layer was separated, washed with saturated brine, then dried over magnesium sulfate, and concentrated under reduced pressure. The residue was purified by silica gel column chromatography (EtOAc/n-hexane) to obtain (5Z)-3-{[t-butyl(diphenyl)silyl]oxy}tetradeca-5-en-1-ol (2.29 g) an oily substance.

Third step: Dichloromethane (120 mL) was added to triphenylphosphine (2.57 g) and dissolved under a nitrogen gas stream, iodine (2.49 g) and imidazole (0.83 g) were added, and the mixture was stirred at room temperature for 10 minutes. A dichloromethane (20 mL) solution of (5Z)-3-{[t-butyl(diphenyl)silyl]oxy}tetradeca-5-en-1-ol (2.29 g) was added, and the mixture was stirred at room temperature for 1 hour. A 5% aqueous sodium thiosulfate solution (100 mL) was added, and the organic layer was separated, then dried over magnesium sulfate, and concentrated under reduced pressure. The residue was purified by silica gel column chromatography (EtOAc/n-hexane) to obtain t-butyl{[(5Z)-1-iodotetradeca-5-en-3-yl]oxy}diphenylsilane (2.61 g) as an oily substance.

Fourth step: A THF (470 mL) solution of methyl 3-sulfanyl propionate (0.59 mL) was ice-cooled under a nitrogen gas stream and sodium hydride (60% dispersion in mineral oil, 220 mg) was added. The mixture was stirred at the same temperature for 15 minutes, and a THF (20 mL) solution of t-butyl{[(5Z)-1-iodotetradeca-5-en-3-yl]oxy}diphenylsilane (2.61 g) was added. After stirring the mixture at the same temperature for 15 minutes, the mixture was stirred at room temperature for 24 hours. The organic layer was separated by adding saturated brine, then dried over magnesium sulfate, and concentrated under reduced pressure. The residue was purified by silica gel column chromatography (EtOAc/n-hexane) to obtain methyl 3-{[(5Z)-3-{[t-butyl(diphenyl)silyl]oxy}tetradeca-5-en-1-yl]sulfanyl}propanoate (1.87 g) as an oily substance.

Fifth step: THF (36 mL) and acetic acid (0.23 mL) were added to methyl 3-{[(5Z)-3-{[t-butyl(diphenyl)silyl]oxy}tetradeca-5-en-1-yl]sulfanyl}propanoate (1.87 g), TBAF (1 M THF solution, 4 mL) was added at room temperature, and the mixture was stirred for 10 hours. Acetic acid (0.45 mL) and TBAF (1 M THF solution, 4 mL) were added, and the mixture was further stirred for 20 hours. The mixture was concentrated under reduced pressure, and the residue was dissolved in ethyl acetate. After the obtained solution was washed twice with water, once with aqueous sodium bicarbonate, and once with saturated brine, the solution was dried over magnesium sulfate and concentrated under reduced pressure. The residue was purified by silica gel column chromatography (EtOAc/n-hexane) to obtain methyl 3-{[(5Z)-3-hydroxytetradeca-5-en-1-yl]sulfanyl}propanoate (0.31 g) as an oily substance.

Sixth step: Under a nitrogen gas stream, methyl of 3-{[(5Z)-3-hydroxytetradeca-5-en-1-yl]sulfanyl}propanoate (150 mg) was dissolved in dichloromethane (3 mL) and ice-cooled. Triethylamine (0.16 mL) and trimethylamine hydrochloride (43 mg) were added and stirred, and chloride (p-toluenesulfonyl) (130 mg) was added little by little. The mixture was stirred at the same temperature for 30 minutes, and water and chloroform were added, followed by extraction with chloroform. The organic layer was washed with aqueous hydrochloric acid solution (1 M), dried over magnesium sulfate, and then concentrated under reduced pressure. The residue was purified by silica gel column chromatography (EtOAc/n-hexane) to obtain methyl 3-({(5Z)-3-[(4-methylbenzene-1-sulfonyl)oxy]tetradeca-5-en-1-yl}sulfanyl)propanoate (148 mg) as an oily substance.

Seventh step: After adsorbing a [$^{18}$F]fluoride ion aqueous solution obtained from a cyclotron onto a pre-conditioned anion exchange resin (Sep-Pak (registered trademark) QMA), a target material was eluted with a mixed solution of 75 mM tetra n-butyl ammonium hydrogencarbonate (0.27 mL) and MeCN (0.7 mL). The eluent was concentrated under reduced pressure at 140° C., MeCN (1 mL) was added, and the eluent was concentrated under reduced pressure at 140° C. MeCN (1 mL) was added again, and the mixture was concentrated under reduced pressure at 120° C. to obtain [$^{18}$F]TBAF. Here, a MeCN (0.8 mL) solution of methyl 3-({(5Z)-3-[(4-methylbenzene-1-sulfonyl)oxy]tetradeca-5-en-1-yl}sulfanyl)propanoate (4 mg) was added and the mixture was heated at 130° C. for 10 minutes. A 0.2 M aqueous potassium hydroxide solution (0.2 mL) was added to the reaction liquid, and the mixture was heated at 110° C. for 4 minutes. A 75% MeCN aqueous solution (1.8 mL) and acetic acid (25 µL) were added to the reaction liquid and the mixture was purified by HPLC (0.005% TFA aqueous solution/0.005% TFA-0.05% D-α-tocopherol-MeCN solution (20:80), column: YMC-Pack Pro C18, S-5 µm, 10×250 mm, flow rate: 6 mL/min). Water (30 mL) was added to the obtained 3-{[(5Z)-3-[$^{18}$F]fluorotetradeca-5-en-1-yl]sulfanyl}propanoic acid fraction, and the solution was allowed to pass through Sep-Pak (registered trademark) Light C18 and washed with a 35% aqueous ethanol solution (5 mL). Subsequently, after eluting the target material with ethanol (1 mL), the solution was allowed to pass through 0.5% Tween (registered trademark) 80-saline (10 mL), was mixed with the above eluent, and was allowed to pass through a sterile filter to obtain a solution containing 3-{[(5Z)-3-[$^{18}$F]fluorotetradeca-5-en-1-yl]sulfanyl}propanoic acid (7-[$^{18}$F]FTO) (22.6 to 37.2 mCi). The generation of the compound was confirmed by the retention time in HPLC being consistent with the time of the non-radiative labeled material shown in Reference Example 1.

Example 2

Reference Example 3 shows a method for synthesizing 5-{[t-butyl(dimethyl)silyl]oxy}-4-{[t-butyl(diphenyl)silyl]oxy}pentanal, which is the starting material in the first step.

First step: 5-[(3Z)-dodeca-3-en-1-yl]-2,2,8,8,9,9-hexamethyl-3,3-diphenyl-4,7-dioxa-3,8-disiladecane was obtained in the same manner as in the first step of Example 1 except that 5-{[t-butyl(dimethyl)silyl]oxy}-4-{[t-butyl(diphenyl)silyl]oxy}pentanal was used as a starting material.

Second step: (5Z)-2-{[t-butyl(diphenyl)silyl]oxy}tetradeca-5-en-1-ol was obtained in the same manner as in the second step of Example 1 except that 5-[(3Z)-dodeca-3-en-1-yl]-2,2,8,8,9,9-hexamethyl-3,3-diphenyl-4,7-dioxa-3,8-disiladecane was used as a starting material.

Third step: t-butyl {[(5Z)-1-iodotetradeca-5-en-2-yl]oxy}diphenylsilane was obtained in the same manner as in the third step of Example 1 except that (5Z)-2-{[t-butyl(diphenyl)silyl]oxy}tetradeca-5-en-1-ol was used as a starting material.

Fourth step: Methyl 3-{[(5Z)-2-{[t-butyl(diphenyl)silyl]oxy}tetradeca-5-en-1-yl]sulfanyl}propanoate was obtained in the same manner as in the fourth step of Example 1 except that t-butyl{[(5Z)-1-iodotetradeca-5-en-2-yl]oxy}diphenylsilane was used as a starting material.

Fifth step: Methyl 3-{[(5Z)-2-hydroxytetradeca-5-en-1-yl]sulfanyl}propanoate was obtained in the same manner as in the fifth step of Example 1 except that methyl 3-{[(5Z)-2-{[t-butyl(diphenyl)silyl]oxy}tetradeca-5-en-1-yl]sulfanyl}propanoate was used as a starting material.

Sixth step: Under a nitrogen gas stream, methyl 3-{[(5Z)-2-hydroxytetradeca-5-en-1-yl]sulfanyl}propanoate (94 mg) was dissolved in dichloromethane (5 mL) and ice-cooled. Triphenylphosphine (112 mg) and carbon tetrabromide (113 mg) was subsequently added and stirred at the same temperature for 1 hour. Water and chloroform were added, followed by extraction with chloroform, drying over magnesium sulfate, and concentration under reduced pressure. The residue was purified by silica gel column chromatography (EtOAc/n-hexane) to obtain methyl 3-{[(5Z)-2-bromotetradeca-5-en-1-yl]sulfanyl}propanoate (36 mg) as a colorless oil.

Seventh step: A solution containing 3-{[(5Z)-2-[$^{18}$F]fluorotetradeca-5-en-1-yl]sulfanyl}propanoic acid (6-[$^{18}$F]FTO) (21.8 mCi) was obtained in the same manner as in the seventh step of Example 1 except that methyl 3-{[(5Z)-2-bromotetradeca-5-en-1-yl]sulfanyl}propanoate was used as a starting material. The generation of the compound was confirmed by the retention time in HPLC being consistent with the time of non-radiative labeled material shown in Reference Example 2.

Example 3

7-[$^{18}$F]FTO can also be obtained by using methyl 3-{[(5Z)-3-bromotetradeca-5-en-1-yl]sulfanyl}propanoate as an intermediate. The steps are shown below.

First step: Methyl 3-{[(5Z)-3-bromotetradeca-5-en-1-yl]sulfanyl}propanoate was obtained in the same manner as in the sixth step of Example 2 except that methyl 3-{[(5Z)-3-hydroxytetradeca-5-en-1-yl]sulfanyl}propanoate was used as a starting material.

Second step: 7-[$^{18}$F]FTO was obtained in the same manner as in the seventh step of Example 1 except that methyl 3-{[(5Z)-3-bromotetradeca-5-en-1-yl]sulfanyl}propanoate was used as a starting material.

Example 4

7-[$^{18}$F]FTO can be obtained by using methyl 3-({(5Z)-3-[(4-nitrobenzene-1-sulfonyl)oxy]tetradeca-5-en-1-yl}sulfanyl)propanoate as an intermediate. The steps are shown below.

First step: Methyl 3-({(5Z)-3-[(4-nitrobenzene-1-sulfonyl)oxy]tetradeca-5-en-1-yl}sulfanyl)propanoate was obtained in the same manner as in the sixth step of Example 1 except that chloride (p-nitrobenzenesulfonyl) was used as a sulfonylating agent and trimethylamine hydrochloride was not used.

Second step: 7-[$^{18}$F]FTO was obtained in the same manner as in the seventh step of Example 1 except that methyl 3-({(5Z)-3-[(4-nitrobenzene-1-sulfonyl)oxy]tetradeca-5-en-1-yl}sulfanyl)propanoate was used as a starting material.

8-[$^{18}$F]FTO was produced in the same manner as in Example 1 except that 5-[(t-butyldimethylsilyl)oxy]-2-[(t-butyldiphenylsilyl)oxy]pentanal was used as a starting material.

The chemical structural formulae and physicochemical data of the compounds obtained in each step are shown in Tables 1 to 3.

TABLE 1

| Ex | Str | | DAT |
|---|---|---|---|
| 1-1 | [structure with OTBDMS and OTBDPS groups] | Me | ESI+: 581 |
| 1-2 | [structure with OH and OTBDPS groups] | Me | ESI+: 489 (M + Na) |
| 1-3 | [structure with I and OTBDPS groups] | Me | NMR (500 MHz): 7.67-7.70 (4H, m), 7.36-7.45 (6H, m), 5.32-5.39 (1H, m), 5.18-5.25 (1H, m), 3.73-3.80 (1H, m), 3.11-3.21 (2H, m), 2.11-2.20 (2H, m), 1.95-2.05 (2H, m), 1.72-1.85 (2H, m), 1.15-1.33 (12H, m,), 1.05 (9H, s), 0.88 (3H, t, J = 7.0 Hz) |
| 1-4 | [structure with S, OMe, O and OTBDPS groups] | Me | ESI+: 591 (M + Na) |
| 1-5 | [structure with S, OMe, O and OH groups] | Me | ESI+: 353 (M + Na) |

TABLE 1-continued

| Ex | Str | DAT |
|---|---|---|
| 1-6 | [structure with OTs, S, C(=O)OMe] | ESI+: 507 (M + Na)<br>NMR (400 MHz): 7.80 (2H, d, J = 8.2 Hz), 7.33 (2H, d, J = 8.2 Hz), 5.41-5.50 (1H, m), 5.16-5.23 (1H, m), 4.60-4.68 (1H, m), 3.70 (3H, s), 2.64-2.74 (2H, m), 2.30-2.57 (9H, m), 1.76-1.98 (4H, m), 1.21-1.32 (12H, m), 0.88 (3H, t, J = 7.0 Hz) |

TABLE 2

| Ex | Str | DAT |
|---|---|---|
| 1-7 | [structure with 18F, S, C(=O)OH] | |
| 2-1 | [structure with OTBDMS, OTBDPS] | CI+: 581 |
| 2-2 | [structure with OH, OTBDPS] | ESI+: 489 (M + Na) |
| 2-3 | [structure with I, OTBDPS] | ESI+: 599 (M + Na) |
| 2-4 | [structure with OTBDPS, S, C(=O)OMe] | ESI+: 591 (M + Na) |
| 2-5 | [structure with OH, S, C(=O)OMe] | ESI+: 353 (M + Na) |
| 2-6 | [structure with Br, S, C(=O)OMe] | ESI+: 415 (M + Na) |

TABLE 3

| Ex | Str | DAT |
|---|---|---|
| 2-7 | [structure with 18F, S, C(=O)OH] | |
| 3-1 | [structure with Br, S, C(=O)OMe] | ACPI/ESI+: 393<br>NMR (500 MHz): 5.51-5.59 (1H, m), 5.36-5.43 (1H, m), 4.09-4.19 (1H, m), 3.71 (3H, s), 2.76-2.83 (3H, m), 2.58-2.70 (5H, m), 2.00-2.09 (4H, m), 1.24-1.41 (12H, m), 0.88 (3H, t, J = 7.0 Hz) |
| 4-1 | [structure with ONos, S, C(=O)OMe] | ESI+: 538 (M + Na)<br>NMR (500 MHz): 8.37-8.41 (2H, m), 8.10-8.14 (2H, m), 5.43-5.50 (1H, m), 5.15-5.21 (1H, m), 4.81-4.86 (1H, m), 3.70 (3H, s), 2.68-2.73 (2H, m), 2.51-2.58 (3H, m), 2.36-2.48 (3H, m), 1.84-1.99 (4H, m), 1.21-1.32 (12H, m), 0.88 (3H, t, J = 7.0 Hz) |

Reference Example 1

3-{[(5Z)-3-fluorotetradeca-5-en-1-yl]sulfanyl}propanoic acid used as a sample of Example 1 was synthesized. The steps are shown below.

Cesium fluoride (69 mg) was heated to 150° C. under reduced pressure, allowed to stand for 2 hours and then allowed to cool. The reaction vessel was purged with nitrogen. AlkylFluor (trademark) (55 mg) was added, and the mixture was allowed to stand at 120° C. under reduced pressure for 1 hour. After the mixture was allowed to cool, toluene (1 mL) was added, and the mixture was stirred at 100° C. for 2 hours. After the mixture was allowed to cool, a toluene (0.8 mL) solution of methyl 3-{[(5Z)-3-hydroxytetradeca-5-en-1-yl]sulfanyl}propanoate (30 mg) was added and the mixture was stirred at 80° C. for 12 hours. The obtained reaction mixture was filtered through celite, the solid was washed with chloroform, and the combined filtrate was concentrated under reduced pressure. The residue was purified by silica gel column chromatography (EtOAc/n-hexane).

THF (0.3 mL) and MeOH (0.9 mL) were added and dissolved in the obtained residue. An aqueous sodium hydroxide solution (1 M, 0.3 mL) was added at room temperature, and the mixture was stirred for 1 hour. After neutralization by adding an aqueous hydrochloric acid solution (1 M), chloroform and saturated brine were added, followed by extraction with chloroform to separate the organic layer. The organic layer was dried over magnesium sulfate and concentrated under reduced pressure to obtain 3-{[(5Z)-3-fluorotetradeca-5-en-1-yl]sulfanyl}propanoic acid (11 mg) as an oily substance.

Reference Example 2

3-{[(5Z)-2-fluorotetradeca-5-en-1-yl]sulfanyl}propanoic acid used as a sample of Example 2 was synthesized. The steps are shown below.

Methyl 3-{[(5Z)-2-hydroxytetradeca-5-en-1-yl]sulfanyl}propanoate (50 mg) was dissolved in toluene (0.5 mL), pyridine-2-sulfonylfluoride (29 mg) and DBU (45 μL) were added at room temperature and the mixture was stirred at room temperature overnight. The reaction liquid was directly purified by silica gel column chromatography (EtOAc/n-hexane).

THF (0.5 mL) and MeOH (0.5 mL) were added and dissolved in the obtained residue. An aqueous sodium hydroxide solution (1 M, 0.5 mL) was added at room temperature, and the mixture was stirred for 30 minutes. After neutralization by adding an aqueous hydrochloric acid solution (1 M), ethyl acetate and saturated brine were added, followed by extraction. The organic layer was dried over magnesium sulfate and concentrated under reduced pressure. The obtained residue was dissolved in water/MeCN solution (20:80, 1 mL) and purified by HPLC (0.005% TFA aqueous solution/MeCN (20:80), column: YMC-Pack Pro C18, 10×250 mm, S-5 μm, flow rate: 6 mL/min). The fraction of the obtained target material was concentrated under reduced pressure to reduce the amount of liquid, and chloroform and saturated brine were added to separate the organic layer. The obtained organic layer was dried over magnesium sulfate and concentrated under reduced pressure, and 3-{[(5Z)-2-fluorotetradeca-5-en-1-yl]sulfanyl}propanoic acid (6.1 mg) was obtained as an oily substance.

Reference Example 3

The method for synthesizing 5-{[t-butyl(dimethyl)silyl]oxy}-4-{[t-butyl(diphenyl)silyl]oxy}pentanal using 6-FTO in Example 2 as a starting material is shown below.

First step: 5-(Benzyloxy)-1-{[t-butyl(dimethyl)silyl]oxy}pentan-2-ol (5.0 g) was dissolved in DMF (10 mL) under a nitrogen gas stream, and imidazole (3.1 g) and t-butyldiphenylsilyl chloride (5.9 mL) were added at room temperature. The mixture was stirred for 72 hours, and water and ethyl acetate were added to separate the organic layer. The organic layer was washed with saturated brine, dried over magnesium sulfate, and concentrated under reduced pressure. The residue was purified by silica gel column chromatography (EtOAc/n-hexane) to obtain 5-[3-(benzyloxy)propyl]-2,2,8,8,9,9-hexamethyl-3,3-diphenyl-4,7-dioxa-3,8-disiladecane (8.28 g) as an oily substance.

Second step: 5-[3-(benzyloxy)propyl]-2,2,8,8,9,9-hexamethyl-3,3-diphenyl-4,7-dioxa-3,8-disiladecane (7.09 g) was dissolved in methanol (140 mL). 10% Pd/C (1.49 g) was added and the reaction vessel was purged with hydrogen. The mixture was stirred for 8 hours. Then, acetic acid (0.7 mL) was added and the mixture was stirred overnight. The mixture was filtered through celite and the filtrate was concentrated under reduced pressure. The residue was purified by silica gel column chromatography (EtOAc/n-hexane) to obtain 5-{[t-butyl(dimethyl)silyl]oxy}-4-{[t-butyl(diphenyl)silyl]oxy}pentan-1-ol (6.12 g) as an oily substance.

Third step: 5-{[t-butyl(dimethyl)silyl]oxy}-4-{[t-butyl(diphenyl)silyl]oxy}pentan-1-ol (2.94 g) was dissolved in dichloromethane (60 mL) and ice-cooled. The Dess-Martin reagent (2.90 g) was added and the mixture was stirred at the same temperature for 1 hour. An aqueous sodium bicarbonate and an aqueous sodium thiosulfate solution were added to separate the solutions. The organic layer was dried over magnesium sulfate and concentrated under reduced pressure. The residue was purified by silica gel column chromatography (EtOAc/n-hexane) to obtain 5-{[t-butyl(dimethyl)silyl]oxy}-4-{[t-butyl(diphenyl)silyl]oxy}pentanal (2.54 g) as an oily substance.

Reference Example 4

[$^{18}$F]FTO was obtained using the same method as the method described in J. Nucl. Med., 2010, 51 (8), 1310-1317, and the solution was prepared in the same manner as in the seventh step of Example 1.

Reference Example 5

First step: 9-Bromononan-4-one (9.8 g) was dissolved in EtOH (160 mL) and ice-cooled. Sodium borohydride (1.7 g) was added little by little, and the mixture was stirred at room temperature for 30 minutes. The mixture was concentrated under reduced pressure, and chloroform was added. The organic layer was washed with water, dried over magnesium sulfate, and concentrated under reduced pressure to obtain 9-bromononan-4-ol (10.23 g) as an oily crude product.

Second step: 9-Bromononan-4-ol (10.2 g) was dissolved in dichloromethane (200 mL) and 3,4-dihydro-2H-pyran (4.35 mL) and pyridinium p-toluenesulfonate (1.15 g) were added. The mixture was stirred at room temperature for 24 hours. 3,4-Dihydro-2H-pyran (3 mL) was added, and the mixture was stirred at room temperature for 16 hours. The solution was washed with aqueous sodium bicarbonate and the organic layer was dried over magnesium sulfate and concentrated under reduced pressure to obtain the residue.

The residue was purified by silica gel column chromatography (EtOAc/n-hexane) to obtain 2-[(9-bromononan-4-yl)oxy]oxane (11.26 g) as an oily substance.

Third step: 2-[(9-Bromononan-4-yl)oxy]oxane (10.57 g), triphenylphosphine (8.58 g), and MeCN (85 mL) were mixed and heated to reflux under a nitrogen atmosphere for 14 hours. The solution was concentrated to obtain {6-[(oxan-2-yl)oxy]nonyl}triphenylphosphineium bromide (19.2 g) as an oily crude product.

Fourth step: t-Butyldimethyl({(5Z)-11-[(oxan-2-yl)oxy]tetradeca-5-en-1-yl}oxy)silane was obtained in the same manner as in the first step of Example 1.

Fifth step: (5Z)-11-[(oxan-2-yl)oxy]tetradeca-5-en-1-ol was obtained in the same manner as in the fifth step of Example 1.

Sixth step: 2-{[(9Z)-14-iodotetradeca-9-en-4-yl]oxy}oxane was obtained in the same manner as in the third step of Example 1.

Seventh step: Methyl 3-({(5Z)-11-[(oxan-2-yl)oxy]tetradeca-5-en-1-yl}sulfanyl)propanoate was obtained in the same manner as in the fourth step of Example 1.

Eighth step: Methyl 3-({(5Z)-11-[(oxan-2-yl)oxy]tetradeca-5-en-1-yl}sulfanyl)propanoate (0.48 g) was dissolved in methanol (25 mL), p-toluenesulfonic acid monohydrate (200 mg) was added, and the mixture was stirred at room temperature for 4 hours. The mixture was concentrated under reduced pressure, aqueous sodium bicarbonate was added, and the mixture was extracted 3 times with chloroform to separate the organic layer. The organic layer was dried over magnesium sulfate and then concentrated under reduced pressure to obtain methyl 3-{[(5Z)-11-hydroxytetradeca-5-en-1-yl]sulfanyl}propanoate (0.43 g) as an oily crude product.

Ninth step: Methyl 3-({(5Z)-11-[(4-methylbenzene-1-sulfonyl)oxy]tetradeca-5-en-1-yl}sulfanyl)propanoate was obtained in the same manner as in the sixth step of Example 1.

Tenth step: A solution of 15-[$^{18}$F]FTO was obtained in the same manner as in the seventh step of Example 1. The generation of the compound was confirmed by comparison with the corresponding non-radiative labeled material (Reference Example 7) as in Example 1.

Reference Example 6

First step: {8-[(Oxan-2-yl)oxy]nonyl}triphenylphosphonium bromide was obtained in the same manner as in the third step of Reference Example 5 except that 2-[(9-bromononan-2-yl)oxy]oxane was used as a starting material.

Second step: t-Butyldimethyl({(5Z)-13-[(oxan-2-yl)oxy]tetradeca-5-en-1-yl}oxy)silane was obtained in the same manner as in the first step of Example 1.

Third step: (5Z)-13-[(oxan-2-yl)oxy]tetradeca-5-en-1-ol was obtained in the same manner as in the fifth step of Example 1.

Fourth step: 2-{[(9Z)-14-iodotetradeca-9-en-2-yl]oxy}oxane was obtained in the same manner as in the third step of Example 1.

Fifth step: Methyl 3-({(5Z)-13-[(oxan-2-yl)oxy]tetradeca-5-en-1-yl}sulfanyl)propanoate was obtained in the same manner as in the fourth step of Example 1.

Sixth step: Methyl 3-{[(5Z)-13-hydroxytetradeca-5-en-1-yl]sulfanyl}propanoate was obtained in the same manner as in the eighth step of Reference Example 5.

Seventh step: Methyl 3-({(5Z)-13-[(4-methylbenzene-1-sulfonyl)oxy]tetradeca-5-en-1-yl}sulfanyl)propanoate was obtained in the same manner as in the sixth step of Example 1.

Eighth step: A solution of 17-[$^{18}$F]FTO was obtained in the same manner as in the seventh step of Example 1. The generation of the compound was confirmed by comparison with the corresponding non-radiative labeled material (Reference Example 8) as in Example 1.

Reference Example 7

3-{[(5Z)-11-fluorotetradeca-5-en-1-yl]sulfanyl}propanoic acid was obtained using the same method as the method described in J. Nucl. Med., 2010, 51 (8), 1310-1317 except that methyl 3-({(5Z)-11-[(4-methylbenzene-1-sulfonyl)oxy]tetradeca-5-en-1-yl}sulfanyl)propanoate was used as a starting material.

Reference Example 8

3-{[(5Z)-13-fluorotetradeca-5-en-1-yl]sulfanyl}propanoic acid was obtained using the same method as the method described in J. Nucl. Med., 2010, 51 (8), 1310-1317 except that methyl 3-({(5Z)-13-[(4-methylbenzene-1-sulfonyl)oxy]tetradeca-5-en-1-yl}sulfanyl)propanoate was used as a starting material.

The chemical structural formulae and physicochemical data of the compounds obtained in Reference Examples 1 to 8 are shown in Tables 4 and 5.

TABLE 4

| Ref | Str | DAT |
|---|---|---|
| 1 | (structure) | ESI−: 317<br>NMR (400 MHz): 5.51-5.57 (1H, m), 5.34-5.42 (1H, m), 4.52-4.71 (1H, m), 2.77-2.83 (2H, m), 2.59-2.76 (4H, m), 2.27-2.50 (2H, m), 2.00-2.05 (2H, m), 1.73-1.99 (2H, m,), 1.22-1.37 (12H, m), 0.88 (3H, t, J = 6.8 Hz) |
| 2 | (structure) | ESI+: 341 (M + Na)<br>NMR (500 MHz): 5.40-5.45 (1H, m), 5.29-35 (1H, m), 4.34-4.70 (1H, m), 2.82-2.89 (2H, m), 2.65-2.80 (3H, m), 2.12-2.31 (2H, m), 1.97-2.10 (2H, m), 1.60-1.83 (2H, m), 1.22-1.33 (13H, m), 0.88 (3H, t, J = 6.9 |

TABLE 4-continued

| Ref | Str | DAT (Hz) |
|---|---|---|
| 3 | [structure: aldehyde with OTBDMS and OTBDPS groups] | ESI+: 493 (M + Na) |
| 4 | [structure: alkene chain with ¹⁸F, thioether, carboxylic acid] | |
| 5 | [structure: alkene chain with Me, ¹⁸F, thioether, carboxylic acid] | |
| 6 | [structure: alkene chain with Me, ¹⁸F, thioether, carboxylic acid] | |

TABLE 5

| Ref | Str | DAT |
|---|---|---|
| 7 | [structure: alkene chain with Me, F, thioether, carboxylic acid] | ESI+: 341 (M + Na) |
| 8 | [structure: alkene chain with Me, F, thioether, carboxylic acid] | ESI+: 341 (M + Na) |

Example 5

PET Test Using Normal Cynomolgus Monkey (Experimental Method)

Solutions containing each compound prepared in Example 1 (7-[$^{18}$F]FTO), Example 2 (6-[$^{18}$F]FTO), Reference Example 4 ([$^{18}$F]FTO), Reference Example 5 (15-[$^{18}$F]FTO), and Reference Example 6 (17-[$^{18}$F]FTO) were used to perform a heart contrast PET test using normal cynomolgus monkeys.

For performing non-invasive PET imaging, in a state in which a male cynomolgus monkey was anesthetized with inhalation anesthetic isoflurane, the monkey was held at a supine body position on a PET camera SHR$_{17000}$ (manufactured by Hamamatsu Photonics K.K.), the solution containing each compound (about 300 MBq) was administered from the lower extremity vein, and continuous imaging was performed for 180 minutes or 240 minutes after the administration. The PET images were reconstructed by dynamic row-action maximum likelihood algorithm (DRAMA) and average images are obtained every 20 minutes. Then, the region of interest (ROI) was set in the heart muscle region or bone (near the spine), and the accumulation (standardized uptake value (SUV)) of each compound was calculated as {radioactivity count in the ROI (MBq/cc)/[dose (MBq)/body weight (g)]}.

(Result)

The SUV values quantified by setting the ROI for the heart muscle and the bone of each compound are shown in Tables 6 and 7 as SUV (heart muscle) and SUV (bone). In the table, Example 1 shows the average of 2 cases, Reference Example 4 shows the average±standard error of 3 cases, and Example 2, Reference Example 5 and Reference Example 6 show the value of 1 case, respectively. A case where the target organ cannot be confirmed in the image and the ROI cannot be set is denoted as n.d, and a case where measurement is not performed is denoted as n.t. In addition, MIP (Maximum Intensity Projection) PET images 60 minutes and 240 minutes after the administration of the compounds of Reference Example 4 ([$^{18}$F]FTO) and Example 1 (7-[$^{18}$F]FTO) are shown in FIG. 1.

femur were isolated 120 minutes after the administration, and the amount of radioactivity was measured with a gamma counter 2480 WIZARD$^2$ (manufactured by PerkinElmer Inc.). The accumulation (SUV) of each compound was calculated as {radioactivity count (MBq/cc)/[dose (MBq)/body weight (g)] in the target organ}.

TABLE 6

| SUV (Heart muscle) | Reference Example 4 [$^{18}$F]FTO | Reference Example 5 15-[$^{18}$F]FTO | Reference Example 6 17-[$^{18}$F]FTO | Example 1 7-[$^{18}$F]FTO | Example 2 6-[$^{18}$F]FTO |
|---|---|---|---|---|---|
| 20 Minutes | 6.45 ± 0.59 | 4.79 | 5.88 | 8.46 | 8.35 |
| 60 Minutes | 6.54 ± 0.51 | 3.60 | 5.78 | 9.26 | 7.25 |
| 120 Minutes | 5.90 ± 0.58 | 3.21 | 4.86 | 8.85 | 6.60 |
| 240 Minutes | 4.63 ± 0.57 | 2.78 | 2.60 | 8.35 | n.t. |

TABLE 7

| SUV (Bone) | Reference Example 4 [$^{18}$F]FTO | Reference Example 5 15-[$^{18}$F]FTO | Reference Example 6 17-[$^{18}$F]FTO | Example 1 7-[$^{18}$F]FTO | Example 2 6-[$^{18}$F]FTO |
|---|---|---|---|---|---|
| 20 Minutes | 1.42 ± 0.10 | 1.27 | 1.11 | n.d. | 1.56 |
| 60 Minutes | 2.27 ± 0.13 | 1.17 | 1.28 | n.d. | 1.96 |
| 120 Minutes | 3.82 ± 0.60 | 1.54 | 1.94 | n.d. | 2.49 |
| 240 Minutes | 6.15 ± 1.02 | 2.10 | 3.23 | n.d. | n.t. |

From the results in Table 6, it was shown that while the accumulation of Reference Example 5 (15-[$^{18}$F]FTO) and Reference Example 6 (17-[$^{18}$F]FTO) to the heart muscle was slightly reduced compared to that of Reference Example 4 ([$^{18}$F]FTO), the accumulation of Example 1 (7-[$^{18}$F]FTO) and Example 2 (6-[$^{18}$F]FTO) to the heart muscle was further increased compared to [$^{18}$F]FTO.

On the other hand, from the results in Table 7, it was shown that the non-specific accumulation of all of 6-[$^{18}$F]FTO, 7-[$^{18}$F]FTO, 15-[$^{18}$F]FTO, and 17-[$^{18}$F]FTO to the bone was equivalent or reduced compared to a case of [$^{18}$F]FTO, particularly, the non-specific accumulation of 7-[$^{18}$F]FTO to the bone was not detected at all, and as shown in FIG. 1, excellent heart PET imaging could be performed.

From these results, it was confirmed that the compounds of Examples of the present invention in which $^{18}$F was substituted at a specific substitution position could achieve both excellent heart accumulation and reduction of non-specific accumulation to the bone.

Example 6

PET Test Using Normal Mouse
(Experimental Method)

A whole body contrast PET test was performed using the solution containing the compound of Example 1 (7-[$^{18}$F]FTO) or Reference Example 4 ([$^{18}$F]FTO) using a DBA2 mouse.

For performing non-invasive PET imaging, in a state in which a male DBA2 mouse was anesthetized with the inhalation anesthetic isoflurane, the mouse was held in a supine body position on a PET camera Inveon (manufactured by Siemens), the solution containing each compound (about 10 MBq) was administered from the tail vein, and after 90 minutes from the administration, PET imaging was performed for 5 minutes. The PET image was reconstructed and then image processing was performed. The heart and (Result)

Figure 2:
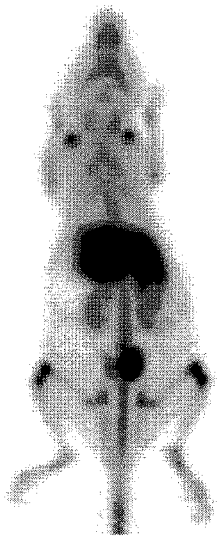
FIG. 2 shows PET images in which the compound ([$^{18}$F] FTO) of Reference Example 4 and the compound (7-[$^{18}$F] FTO) of Example 1 are administered to normal mice in Example 6, respectively. PET images 90 minutes after administration of [$^{18}$F]FTO and 7-[$^{18}$F]FTO are shown in (A) and (B), respectively.
Figure 2:
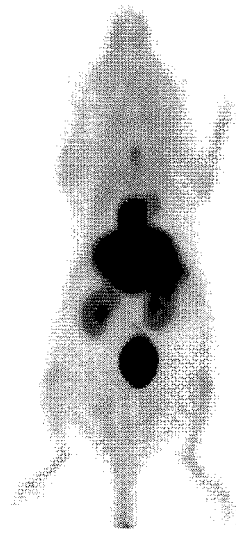

Whole body PET images 90 minutes after the administration are shown in FIG. 2. Table 8 shows the SUV values (average value±standard error) in each of 5 cases in which the amount of radioactivity in the target organ is quantified 120 minutes after the administration.

TABLE 8

| SUV | Reference Example 4 [$^{18}$F]FTO | Example 1 7-[$^{18}$F]FTO |
|---|---|---|
| Heart | 1.52 ± 0.25 | 3.53 ± 0.77 |
| Femur | 2.03 ± 0.32 | 0.48 ± 0.04 |

From the results in Table 8 above, it was confirmed that the compound of Example 1 (7-[$^{18}$F]FTO) had excellent accumulation to the heart and low non-specific accumulation in the bone compared to the compound of Reference Example 4 ([$^{18}$F]FTO) by measurement using the extracted organs. This is also confirmed from the whole body MIP PET images of FIG. 2.

Example 7

PET Test Using Model Rat with Myocardial Infarction by Coronary Artery Ligation
(Experimental Method)

A myocardial infarction model was prepared by coronary artery ligation using SD rats, and a thoracic contrast PET test was performed using the solution containing the compound of Example 1 (7-[$^{18}$F]FTO).

In a state in which an untreated rat or a model rat with myocardial infarction was anesthetized with the inhalation anesthetic isoflurane using a male SD rat, the rat was held in a supine body position on a PET camera Inveon (manufactured by Siemens), and the solution containing the compound (about 10 MBq) was administered from the tail vein. After 20 minutes from the administration, PET imaging was performed for 5 minutes. The PET image was reconstructed and then image processing was performed.

(Result)

Figure 3:
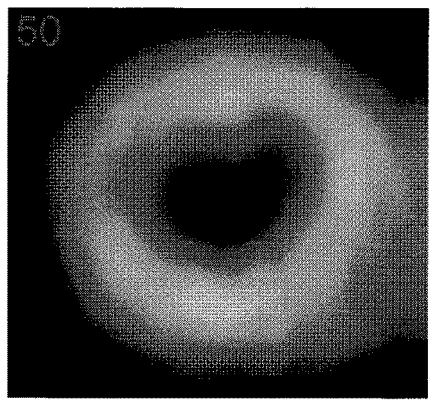
FIG. 3 shows PET images in which the compound (7-[$^{18}$F]FTO) of Example 1 is administered to a normal rat and a myocardial infarction model rat in Example 7. The PET cross-sectional images of the hearts of a normal rat and a myocardial infarction model rat 20 minutes after administration of 7-[$^{18}$F]FTO are shown in (A) and (B), respectively.
Figure 3:
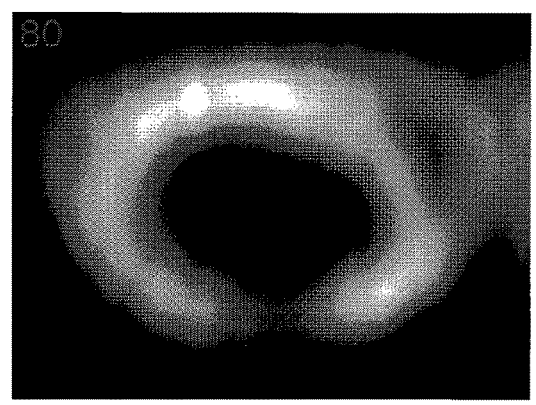

FIG. 3 shows coronal section PET images of the compound near the center of the heart in the untreated rat or the model rat with myocardial infarction.

In FIG. 3, it was confirmed that while an elliptical heart was visualized in the coronal section image of the untreated rat (A), the signal was deleted in a part of the elliptical heart in the coronal section image of the myocardial infarction model rat (B). It was considered that the deletion of this signal indicated that myocardial infarction by coronary artery ligation was caused myocardial metabolic insufficiency and it was suggested that this compound was effective in diagnosing heart disease typified by myocardial infarction.

INDUSTRIAL APPLICABILITY

The labeled fatty acid derivative of the present invention can be used as a radiolabeled tracer for rapid and non-invasive sorting of heart disease patients, diagnosis of the therapeutic effect of a therapeutic drug for heart disease, and the like.

The invention claimed is:

1. A labeled fatty acid derivative represented by formula (I) or a salt thereof,

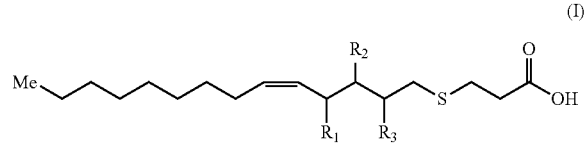

(in the formula, any one of $R_1$ to $R_3$ is $^{18}F$, the other two are H, and Me is a methyl group).

2. The labeled fatty acid derivative or a salt thereof according to claim 1, wherein $R_1$ is H.

3. The labeled fatty acid derivative or a salt thereof according to claim 1, wherein the labeled fatty acid derivative is 3-{[(5Z)-3-[$^{18}F$]fluorotetradeca-5-en-1-yl]sulfanyl}propanoic acid.

4. The labeled fatty acid derivative or a salt thereof according to claim 1, wherein the labeled fatty acid derivative is 3-{[(5Z)-2-[$^{18}F$]fluorotetradeca-5-en-1-yl]sulfanyl}propanoic acid.

5. A composition for diagnostic imaging comprising:
the labeled fatty acid derivative or a salt thereof according to claim 1; and
a pharmaceutically acceptable carrier.

6. A method for diagnostic imaging of heart disease comprising: administering a detectable amount of the labeled fatty acid derivative or a salt thereof according to claim 1 to a subject.

7. The method for diagnostic imaging according to claim 6, wherein the heart disease is an ischemic heart disease.

8. A method for producing the labeled fatty acid derivative or a salt thereof according to claim 1, comprising:
allowing a [$^{18}F$]fluoride ion to react with the compound represented by formula (1i) or a salt thereof:

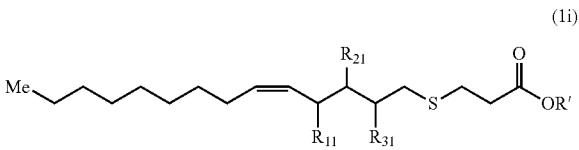

(in the formula, any one of $R_{11}$ to $R_{31}$ is a leaving group, the other two are H, and R' is an H or a lower alkyl group which may be substituted, and Me is a methyl group.

9. The composition for diagnostic imaging according to claim 5, wherein the labeled fatty acid derivative is 3-{[(5Z)-3-$^{18}F$ fluorotetradeca-5-en-1-yl]sulfanyl}propanoic acid.

10. The composition for diagnostic imaging according to claim 5, wherein the labeled fatty acid derivative is 3-{[(5Z)-2-$^{18}F$ fluorotetradeca-5-en-1-yl]sulfanyl}propanoic acid.

11. The method for diagnostic imaging according to claim 6, wherein the labeled fatty acid derivative is 3-{[(5Z)-3-$^{18}F$ fluorotetradeca-5-en-1-yl]sulfanyl}propanoic acid.

12. The method for diagnostic imaging according to claim 6, wherein the labeled fatty acid derivative is 3-{[(5Z)-2-$^{18}F$ fluorotetradeca-5-en-1-yl]sulfanyl}propanoic acid.

13. The method for diagnostic imaging according to claim 6, wherein further comprising the step of imaging the labeled fatty acid derivative or a salt thereof in the heart of the subject.

14. The method for diagnostic imaging according to claim 13, where the imaging is by positron emission tomography (PET).

* * * * *

UNITED STATES PATENT AND TRADEMARK OFFICE
CERTIFICATE OF CORRECTION

| | |
|---|---|
| PATENT NO. | : 12,029,797 B2 |
| APPLICATION NO. | : 17/261328 |
| DATED | : July 9, 2024 |
| INVENTOR(S) | : Murakami et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 794 days.

Signed and Sealed this
Twelfth Day of November, 2024

Katherine Kelly Vidal
*Director of the United States Patent and Trademark Office*